United States Patent [19]

Bianchetti et al.

[11] Patent Number: 4,735,947
[45] Date of Patent: Apr. 5, 1988

[54] METHYLLEVALLORPHANIUM SALTS HAVING PERIPHERAL OPIATE ANTAGONISTIC ACTIVITY

[75] Inventors: Alberto Bianchetti, Milan; Dino Nisato, Pavia; Luciano Manara, Pietra Marazzi; Roberto Sacilotto, Milan, all of Italy

[73] Assignee: Sanofi, France

[21] Appl. No.: 825,798

[22] Filed: Feb. 4, 1986

Related U.S. Application Data

[63] Continuation of Ser. No. 622,498, Jun. 20, 1984, abandoned.

[30] Foreign Application Priority Data

Jun. 24, 1983 [FR] France ................ 83 10526

[51] Int. Cl.$^4$ ................ A61K 31/485; C07D 221/28
[52] U.S. Cl. ........................ 514/289; 546/74
[58] Field of Search ............ 546/74; 514/289

[56] References Cited

U.S. PATENT DOCUMENTS

3,101,339 8/1963 Zeile et al. ................ 546/44
4,176,186 11/1979 Goldberg et al. ............ 574/289
4,489,079 12/1984 Giudice et al. ............. 514/289

FOREIGN PATENT DOCUMENTS

0077723 4/1983 European Pat. Off. ........... 424/260
1179915 5/1959 France .

OTHER PUBLICATIONS

Kobylecki et al., J. Med. Chem., vol. 25(11), pp. 1278-1280, (11/82).
Bianchetti et al., Life Sci., vol. 31(20-21), pp. 2261-2264, (1982).
Bianchetti et al., Life Sci., vol. 33(suppl. 1), pp. 415-418, (1983).
Dragonetti et al., Life Sci., vol. 33(suppl. 1), pp. 477-480, (1983).
Barton et al., ed., "Synthetic Analgesics", Pergamon Press (1974), part II, p. 48.
Koczka et al., Chemical Abstracts, vol. 67, 11621n, (1967).
Hellerbach et al., Helv. Chim. Acta, vol. 39(49) fasc II, pp. 429-440, (1956).
Notarnicola et al., Chemical Abstracts, vol. 100, 17504y, (01/16/84).
International Series of Monographs in Organic Chemistry, Barton et al., General Editors, vol. 8, Synthetic Analgesics, Part IIA, Morphinans, by Hellerbach et al., Pergamon Press, N.Y., (1966), pp. 3-112.

*Primary Examiner*—Donald G. Daus
*Assistant Examiner*—Diana G. Rivers
*Attorney, Agent, or Firm*—Bacon & Thomas

[57] ABSTRACT

Methyllevallorphanium salts having peripheral antagonistic activity of formula

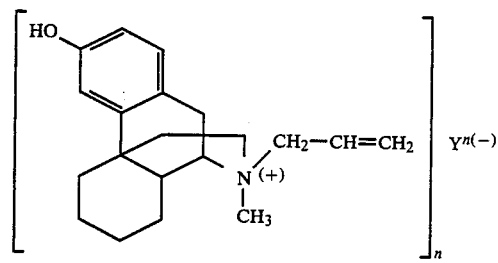

wherein $Y^{n(-)}$ represents the anion a pharmaceutically acceptable acid other than halogen and n represents the number of negative charges of said anion; a process for their preparation by exchange of the halogen ion with the $Y^{n(-)}$ anion; and pharmaceutical compositions containing them as active ingredients.

14 Claims, No Drawings

METHYLLEVALLORPHANIUM SALTS HAVING PERIPHERAL OPIATE ANTAGONISTIC ACTIVITY

This application is a continuation of application Ser. No. 622,498, filed on June 20, 1984, now abandoned.

The present invention relates to peripheral opiate antagonists.

More particularly, the present invention concerns quaternary salts derivatives of (—)-3-hydroxy-N-allyl-morphinan, herein designated by its International Non-proprietary Name "levallorphan".

Despite the various problems associated with the use of opiates, such as tolerance and physical dependence, morphine-like drugs remain the products of choice in the treatment of severe pain.

An often serious side effect of morphine-like drugs is constipation, which is due to their local action on the intestinal opiate receptors.

To palliate this type of side effect, which is distressing to the patient, it has been proposed that a narcotic antagonist having a weak capacity of crossing the blood-brain barrier could significantly reduce the constipation induced by the morphine-like drugs without substantially reducing the analgesic effects thereof.

The U.S. Pat. No. 4,176,186 describes quaternary derivatives of morphine-like antagonists which prevent or eliminate the side effects of opiates on the intestinal motility. Among the compounds claimed in said Patent, the preferred compounds are the quaternary derivatives of N-allylnoroxymorphone, hereinafter designated "naloxone", among which the bromomethylate is particularly preferred.

Another compound, levallorphan bromoallylate, has been described as peripheral narcotic antagonist (Life Sci. 1982, 31, 2261-2264).

According to French patent application No. 82,22 133 filed on Dec. 30, 1982, the reaction of levallorphan with a methyl halide gives a compound designated "levallorphan halomethylate" of formula

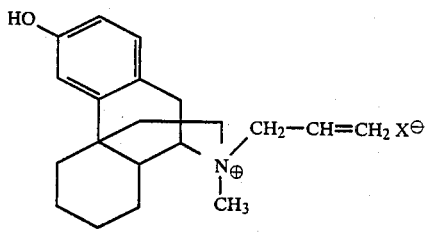

I wherein X represents chlorine, bromine or iodine, which has practically no ability to pass through the blood-brain barrier although it maintains a very good peripheral antagonistic activity.

The term "levallorphan halomethylate" is used in the above mentioned patent application to distinguish the product prepared as described hereinabove from the compound obtained by the reaction of an allyl halide with (—)-3-hydroxy-N-methylmorphinan, having the International Non-proprietary Name "levorphanol". This latter also possess the formula I above, but it shows different physicochemical characteristics and is devoid of both peripheral and central opiate antagonistic activity.

Quaternization of the nitrogen atom in 17-position introduces, indeed, a new asymmetry center and the two diastereoisomers can be obtained by differentiated synthesis as indicated hereinabove as well as in J. Med. Chem. 1982, 25, 1278-1280 where the preparation of two diastereoisomeric compounds derived from nalorphine and morphine, respectively, is described.

Levallorphan halomethylates described in the above mentioned French patent application, however, present some problems due to the particular characteristics of the products; for example the use of a product having a "I—" ion in a drug implies the control of the thyroid function of the patients. On the other side, the compounds bearing the Cl— and Br— ions, imply, in their preparation, the use of methyl bromide and chloride which are gaseous products, and not easily handled.

It has now been found that by reacting a levallorphan halomethylate with an excess of a pharmaceutically acceptable acid there is obtained the exchange of the halogen ion for the anion of the acid used and the formation of new (—)-3-hydroxy-N-methyl-N-allylmorphinanium salts having the same configuration of the starting levallorphan halomethylate and which are designated hereinafter "methyllevallorphanium salts".

It has also been found that the new salts thus obtained, possess, they too, a good peripheral opiate antagonistic activity and practically no capacity of crossing the blood-brain barrier.

Thus, it is an object of the present invention, to provide methyllevallorphanium salts of formula

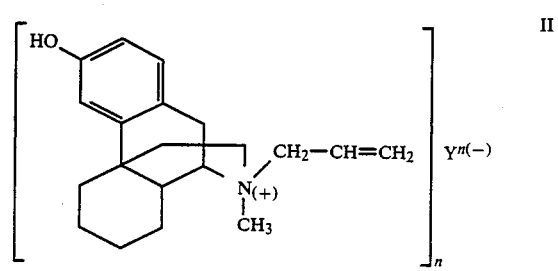

II wherein $Y^{n(-)}$ represents the anion of a pharmaceutically acceptable acid other than halogen anion and n represents the number of negative charges of said anion.

The anion of the pharmaceutically acceptable acid originates from whatever acid generally used to salify the compounds intended for pharmaceutical purposes and particularly the acid salifying the opiates.

The methanesulfonic, ethanesulfonic, p-toluenesulfonic, 2-naphtalenesulfonic, 1,5-naphtalenedisulfonic, sulfuric, sulfuric monomethylester, phosphoric, ascorbic, malonic, maleic, tartaric, fumaric, malic, phytic, citric, succinic, 4,4-methylene-bis-(3-hydroxy-2-naphtoic) acids are advantageous salifying acids.

The anions methanesulfonate ($CH_3SO_3-$), hereinafter referred to as "mesilate", p-toluenesulfonate ($4CH_3-C_6H_4SO_3-$) hereinafter referred to as "tosilate", 2-naphtalenesulfonate ($2-C_{10}H_7SO_3-$), hereinafter referred to as "napsilate", hydrogen maleate (cis-$HOOC-CH=CH-COO-$), neutral sulfate ($SO_4^{2-}$), hereinafter referred to as "sulfate", and methylsulfate ($CH_3O-SO_3-$) are particularly preferred.

The methyl levallorphanium salts of the present invention are prepared, according to another aspect of the present invention, by exchanging the halogen ion of a levallorphan halomethylate, preferably the iodomethylate, for the $Y^{n(-)}$ anion of a pharmaceutically acceptable acid, for example by means of an ion exchange resin.

A resin of the AMBERLITE (registered trademark) series, particularly AMBERLITE IRA-400 bearing the chloride anion, is preferably used. The chlorine ion is shifted by passing a solution of an alkaline hydroxide through a column containing the resin and the column is washed thoroughly with distilled water up to neutral pH. Then a 10% aqueous solution of the selected pharmaceutically acceptable acid is passed through the column containing the neutral resin and washed again with distilled water up to neutral pH to obtain the resin bearing the anion of the acid used.

An aqueous solution of levallorphan halomethylate is passed through the column so prepared and eluted with water.

The methyl levallorphanium salt thus obtained is isolated by evaporating the aqueous solution to dryness and by crystallizing from an appropriate solvent.

The antagonism to the peripheral action of opiates is assessed on the basis of the percent inhibition of the analgesic and of the constipating effects of morphine. The ratio between the dose which inhibits by 50% the analgesic effect of morphine and the dose which inhibits by 50% its constipating effect represents the index of the peripheral activity.

The antagonism to the analgesic effect of morphine was assessed by the hot-plate analgesia test according to P. A. Janssen et al. (J. Pharm. Pharmacol. 1957, 9, 381–400) by using fasting (18 hours) female mice of 20-22 g. Morphine was injected subcutaneously (24 mg/kg) thirty minutes before the beginning of the test. The antagonist was injected subcutaneously 5 minutes before the morphine. The antagonistic activity was expressed as ID50 of the morphine antinociceptive effect, calculated on the basis of the log dose reaction time regression of the animals treated with different doses of the products under testing.

The antagonism to the morphine constipating effect of the methyl levallorphanium salts of the present invention was assessed according to the test described by A. F. Green (Br. J. Pharm. Chemother. 1959, 14, 26–34), slightly modified.

Three groups of fasting (20 hours) female mice of about 20 g were used. To a control group, a meal consisting of 0.2 ml of a mixture of 5% arabic gum (6 ml), flour (2 g) and charcoal (1 g) was administered by oral route. The second group was treated with 12 mg/kg of morphine s.c. and, immediately afterwards, with the above charcoal meal. The third group was treated with the antagonist under examination by subcutaneous route, then, after 5 minutes, with 12 mg/kg of morphine by subcutaneous route and, immediately afterwards, with the charcoal meal. After 30 minutes, the animals were sacrificed to assess the portion of intestine through which the charcoal had passed, expressed as percent of the total length of the small intestine.

The doses which inhibit by 50% the analgesic effect (ID50a) and the constipating effect (ID50c) have been extrapolated from least square log dose-response line by applying the analysis of the variance by linear regression.

The results obtained in the above described test for two representative compounds of the present invention, namely methyl levallorphanium methylsulfate and methyllevallorphanium mesilate and for four reference compounds, namely levallorphan bromoallylate described in Life Sci. 1982, 31, 2261–2264, naloxone sulfomethylate, described in U.S. Pat. No. 4,176,186, levallorphan tartrate and naloxone are summarized in Table I.

TABLE I

| Compound | Antagonism to the analgesic effect ID50a (mg/kg) | Antagonism to the constipating effect ID50c (mg/kg) | ID50a/ ID50c |
|---|---|---|---|
| methyllevallorphanium methylsulfate | ~60* | 4.9 (2.9–8.6) | ~12 |
| methyllevallorphanium mesilate | >60 | 7.4 (4.4–12.6) | >8 |
| levallorphan bromoallylate | 15.2 (9.7–24) | 15.65 (8.46–28.9) | 0.97 |
| naloxone sulfomethylate | 1.6 (0.7–3.6) | 5.8 (2.9–11.5) | 0.27 |
| levallorphan tartrate | 0.03 (0.01–0.08) | 5.5 (1.7–17.8) | 0.01 |
| naloxone | 0.06 (0.02–0.15) | 0.75 (0.46–1.23) | 0.08 |

*ID50 not determinable (at 30 mg/kg: inhib. 41%) (at 60 mg/kg: inhib. 49%)

It results from this table that the representative compounds of the invention antagonize the constipating effect of morphine with an ID50c of 4.9 mg/kg and 7.4 mg/kg, respectively, whilst one of them antagonizes the analgesic effect of morphine at the maximal injectable doses only and the other does not antagonize it even at the maximal injectable dose. On the contrary, the quaternary derivative of naloxone described in U.S. Pat. No. 4,176,186 does not possess any satisfactory peripheral selectivity.

Actually, in these experimental conditions it is more active against the analgesic effect than against the constipating effect of morphine.

As for levallorphan bromoallylate, it is a good opiate peripheral antagonist, but the ratio between its ID50a and ID50c is by far lower than that of the compounds of the present invention.

Naloxone and levallorphan tartrate are more active as antagonists of the analgesic effect than as antagonists of the constipating effect.

For their selective peripheral antagonistic action and their only slight toxicity, the levallorphanium salts of the present invention are useful as drugs.

Thus, it is a further object of the present invention to provide pharmaceutical compositions having a peripheral opiate antagonistic activity containing, as active ingredient, a methyllevallorphanium salt of formula II in admixture with a pharmaceutical carrier.

The pharmaceutical compositions of the present invention, having peripheral opiate antagonistic action, are useful in the treatment of pathological conditions where there are altered rates of exogenous or endogenous opiates, or a hypersensitivity to opiates outside the central nervous system of mammals.

Thus, the compositions of the present invention may be administered to mammals, animals and human beings, with opiates in order to prevent the side effects, especially constipation, which derive in particular from the activation of the peripheric opiate receptors without affecting analgesia, or any other action induced by the stimulation of the central receptors by the opiate.

In order to obtain the desired peripheral antagonistic effect, the daily dose of active ingredient may vary between 0.05 and 200 mg per kg of body-weight.

Each dosage unit may contain from 1 to 500 mg of active ingredient in admixture with a pharmaceutical carrier. This dosage unit may be administered to the mammals 1 to 4 times per day.

The pharmaceutical compositions of the present invention having a peripheral opiate antagonistic action may be formulated for oral, sublingual, nasal, subcutaneous, intramuscular, intravenous, transdermal or rectal administration, by mixing the active ingredient of formula II hereinabove with conventional pharmaceutical carriers.

The dosage unit forms include tablets, capsules, powders, granules and oral solutions or suspensions, suppositories and ampoules for parenteral administration.

When a solid composition is prepared in the form of tablets, the main active ingredient is mixed with a pharmaceutical carrier such as gelatine, starch, lactose, magnesium stearate, talc, arabic gum or the like. The tablets may be coated with saccharose or other appropriate substances or they may be treated so that their activity is extended or delayed and that they continuously release a predetermined amount of active ingredient.

A preparation in capsules is obtained by mixing the active ingredient with a diluent and by pouring the mixture obtained in soft or hard capsules.

A preparation in the form of syrup or elixir may contain the active ingredient jointly with a sweetening agent, acaloric if necessary, methylparaben and propylparaben as antiseptics, as well as a flavoring agent and an appropriate dye.

Water-dispersible powders or granulates may contain the active ingredient mixed with dispersing agents or wetting agents, or suspending agents such as polyvinylpyrrolidone and the like, and with sweetening or flavoring agents as well.

For rectal administration, suppositories are prepared with binding agents melting at rectal temperature, for example, cocoa butter or polyethyleneglycols.

For oral administration in drops or for parenteral administration, aqueous suspensions, isotonic saline solutions or sterile injectable solutions are used, which contain pharmacologically compatible dispersing and/or wetting agents, for example propyleneglycol or butyleneglycol.

The active ingredient may also be formulated in the form of microcapsules, possibly with one or more carriers or additives.

The compositions of the present invention may contain, in addition to the methyllevallorphanium salt, other active ingredients such as, for example, an analgesic opiate agonist or agonist/antagonist, such as morphine, codeine, buprenorphine and the like, antitussives or other appropriate drugs.

The following examples illustrate the invention without, however, limiting it.

PREPARATION

A mixture of 5 g of levallorphan, 70 ml of dimethylformamide and 6.7 g of methyl iodide, is heated under stirring for 6 hours at the external temperature of 80° C., then it is concentrated under reduced pressure while eliminating the solvent and the excess of alkylating agent by addition of acetone. By cooling the acetone solution a solid product is obtained which, after filtration and drying under reduced pressure, melts at 225°–227° C. By recrystallization from 50 ml of 90% ethanol, 5 g of a white product are obtained; m.p. 230°–232° C. After two further crystallizations up to a constant rotatory power, pure levallorphan iodomethylate is obtained; yield 40%; m.p. 232°–234° C. (Tottoli method); $[\alpha]_D^{20} = -64° \pm 1°$ (methanol, c=0.2%).

The protonic NMR spectrum obtained at 250 MHz in deuterated dimethylsulfoxide, by using tetramethylsilane as internal standard, presents a singlet at 3.20±0.02 ppm, relative to the methyl group in the 17 position.

The other diastereoisomer, namely levallorphanol iodoallylate, presents the same singlet at 3.04±0.02 ppm

EXAMPLE 1

In a glass column, 2.5 cm in diameter, are introduced 100 g of ion exchange resin AMBERLITE IRA-400 (registered trademark, B.D.H.) in the form of hydrochloride. After elution with 1000 ml of 10% sodium hydroxide, the mixture is washed with distilled water up to neutral pH, eluted with a 10% methanesulfonic acid solution up to acid pH, then washed again with water up to neutral pH. On the column, containing the resin in the mesilate form thus obtained, is poured a solution of 3 g of levallorphan iodomethylate (described in the PREPARATION) in distilled water, then it is eluted with water. The water is evaporated to dryness under reduced pressure and the residue is crystallized from ethanol. Thus, 2 g of methyllevallorphanium mesilate (formula II, $Y^{n(-)} = CH_3SO_3^-$) are obtained; m.p. 265°–267° C.; $[\alpha]_D^{20} = -64.9°$ (c=0.5% methanol).

EXAMPLE 2

By operating as described in Example 1, by exchanging the $I^-$ ion of the levallorphan iodomethylate (3 g) for the methylsulfate ion on an AMBERLITE IRA-400 column traited with sulfuric acid monomethyl ester, 1.9 g of methyllevallorphanium methylsulfate are obtained (formula II, $Y^{n(-)} = CH_3OSO_3^-$); m.p. 263°–265° C.; $[\alpha]_D^{20} = -63.8°$ (c=0.5% methanol).

EXAMPLE 3

By operating as described in Example 1, starting from 3 g of levallorphan iodomethylate, on a column containing AMBERLITE IRA-400 resin, treated with maleic acid, 2.1 g of methyllevallorphanium hydrogen maleate (formula II, $Y^{n(-)} = $ cis-HOOC—CH=CH—COO$^-$) crystallized from isopropanol are obtained; m.p. 209°–211° C., $[\alpha]_D^{20} = -61.2°$ (c=0.5% methanol).

EXAMPLES 4 TO 7

By operating as described in Example 1, starting from 3 g of levallorphan iodomethylate, on a column containing AMBERLITE IRA-400 resin, treated with fumaric acid, L(+)tartaric acid, perchloric acid and, respectively, phosphoric acid, the following levallorphanium salts are obtained methyllevallorphanium hydrogen fumarate (formula II, $Y^{n(-)} = $ trans-HOOC—CH=CH—COO$^-$); m.p. 235° C. (dec); $[\alpha]_D^{20} = -63.6°$ (c=0.5% methanol); Ex. 4;

methyllevallorphanium hydrogen L(+)tartrate (formula II, $Y^{n(-)} = $ L(+)-HOOC—CHOH—CHOH—COO$^-$); m.p. 223°–225° C.; Ex. 5;

methyllevallorphanium perchlorate (formula II, $Y^{n(-)} = ClO_4^-$); m.p. 258°–260° C.; $[\alpha]_D^{20} = -65.3°$ (c=0.5% methanol); Ex. 6;

methyllevallorphanium dihydrogen phosphate (formula II, $Y^{n(-)} = H_2PO_4^-$); m.p. 235°–237° C.; $[\alpha]_D^{20} = -62.5°$ (c=0.5% methanol); Ex. 7;

EXAMPLE 8

Tablets containing a methyllevallorphanium salt according to Examples 1 to 7 as active ingredient, have the following composition:
active ingredient: 50 mg
lactose: 145 mg
avicel: 100 mg
magnesium stearate: 5 mg The active ingredient is crushed to a particle dimension of 0.4 mm size, by passing it through a 0.4 mm sieve, by mixing the crushed mixture with the other constituents and compressing to form tablets.

In the same manner, tablets containing 40 mg of active ingredient are prepared.

EXAMPLE 9

Capsules containing a methyllevallorphanium salt according to Examples 1 to 7 as active ingredient, have the following composition:
active ingredient: 15 mg
lactose: 120 mg
magnesium stearate: 5 mg Charges of the ingredients above are mixed intimately and the mixture is poured into hard gelatine capsules.

In the same way, capsules containing 25 mg of active ingredient are prepared.

EXAMPLE 10

10,000 capsules with a content of active substance of 50 mg are prepared from the following constituents: 500 g of a methyllevallorphanium salt according to Examples 1 to 7, 495 g of microcrystalline cellulose, 5 g of amorphous silica gel. The above constituents are mixed intimately and introduced into capsules of hard gelatin of dimension 4.

EXAMPLE 11

A sterile aqueous solution useful for parenteral use and having the following composition:
methyllevallorphanium mesilate: 10 mg
water for injectable preparation to 2 ml
is prepared and introduced into sterile ampoules.

In the same manner, a sterile solution containing 10 mg of a methyllevallorphanium salt according to Examples 2 to 7 is prepared and introduced into sterile ampoules.

EXAMPLE 12

Suppositories containing a methyllevallorphanium salt according to Examples 1 to 7 as active ingredient have the following composition:
active ingredient: 50 mg
lactose: 250 mg
mass for suppositories to 1.7 g The active ingredient is mixed with the lactose and the mixture is placed uniformly in suspension in the molten mass for suppositories. The suspension is poured into cooled moulds to form suppositories weighing 1.7 g.

EXAMPLE 13

Sugar-coated tables each containing 30 mg of a methyllevallorphanium salt according to Examples 1 to 7 as active ingredient are prepared, using talc, lactose, corn starch, sodium alginate, caster sugar, granulated sugar, magnesium stearate, white shellac, gelatin for food, erythrosin, titanium dioxide and white wax as appropriate carriers.

We claim:

1. A methyllevallorphanium salt of formula

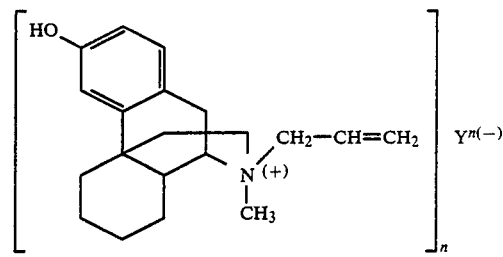

wherein $Y^{n(-)}$ represents an anion of a pharmaceutically acceptable acid which is methanesulfonic, ethanesulfonic, p-toluenesulfonic, 2-naphtalenesulfonic, 1,5-naphtalenedisulfonic, sulfuric, sulfuric-monomethylester, phosphoric, ascorbic, malonic, maleic, tartaric, fumaric, malic, phytic, citric, succinic or 4,4-methylene-bis-(3-hydroxy-2-naphtoic) acid; and n represents the number of negative charges of said anion; said compounds having a ID50a/ID50c ratio of greater than 8.

2. The compound of claim 1 which is methyllevallorphanium mesilate.

3. Methyllevallorphanium hydrogen maleate.

4. The compound of claim 1 which is methyllevallorphanium methylsulfate.

5. A pharmaceutical composition having peripheral opiate antagonistic activity, comprising, as active ingredient, a compound as claimed in claim 1.

6. A pharmaceutical composition as claimed in claim 5 in dosage unit form.

7. A pharmaceutical composition as claimed in claim 6 which comprises from 1 to 500 mg of active ingredient in admixture with a pharmaceutical carrier.

8. A pharmaceutical composition having peripheral opiate antagonistic activity, comprising, as active ingredient, a compound as claimed in claim 2.

9. A pharmaceutical composition having peripheral opiate antagonistic activity, comprising, as active ingredient, a compound as claimed in claim 3.

10. A pharmaceutical composition having peripheral opiate antagonistic activity, comprising, as active ingredient, a compound as claimed in claim 4.

11. A method of preventing constipation caused by an opiate without affecting the analgesia caused by said opiate in a mammal which comprises administering to said mammal an effective amount of the compound of claim 2 in combination with a pharmaceutical carrier.

12. The compound of claim 1 having an ID50a/ID50c ratio of greater than 8.

13. A pharmaceutical composition as claimed in claim 2 wherein the methyllevallorphanium mesilate has an ID50a/ID50c ratio greater than 8.

14. A pharmaceutical composition as claimed in claim 4 wherein the methyllevallorphanium has an ID50a/ID50c ratio of about 12.

* * * * *